United States Patent [19]

Mucci et al.

[11] Patent Number: 5,608,326
[45] Date of Patent: Mar. 4, 1997

[54] PLASTICS IDENTIFICATION

[75] Inventors: Peter E. R. Mucci, Durley; Graham L. Hearn, Highfield; Ann M. Eyers, Kent Road, all of United Kingdom

[73] Assignee: Ford Motor Company, Dearborn, Mich.

[21] Appl. No.: 491,970

[22] PCT Filed: Jan. 19, 1994

[86] PCT No.: PCT/GB94/00101

§ 371 Date: Jul. 21, 1995

§ 102(e) Date: Jul. 21, 1995

[87] PCT Pub. No.: WO94/17402

PCT Pub. Date: Aug. 4, 1994

[30] Foreign Application Priority Data

Jan. 21, 1993 [GB] United Kingdom .................. 9301128
Jun. 5, 1993 [GB] United Kingdom .................. 9311679

[51] Int. Cl.$^6$ ................................................. G01R 27/26
[52] U.S. Cl. .......................... 324/454; 324/452; 324/71.1
[58] Field of Search .............................. 324/454, 452, 324/451, 457, 71.1, 464; 209/571, 3.1

[56] References Cited

U.S. PATENT DOCUMENTS 3,733,544  5/1973  Petrick .
4,685,569  8/1987  Osaki .
5,341,103  8/1994  Dasgupta et al. ........................ 324/454
5,455,514  10/1995  Pazda et al. ............................ 324/454

FOREIGN PATENT DOCUMENTS 52-086452  7/1977  Japan .
1184419  3/1970  United Kingdom .
2221310  1/1990  United Kingdom .

OTHER PUBLICATIONS

Journal of Physics vol. 9, No. 3, pp. 226–229 Mar. 1976; Ohara et al.; Apparatus for Simultaneous Measurements of Static Electricity and Friction of Polymer Films.

Textile Research Journal, vol. 24, No. 9; Sep. 1954 Kirkwood et al.; Measurement of Triboelectric Response of Raw Cottons.

Primary Examiner—Maura K. Regan
Attorney, Agent, or Firm—Damian Porcari

[57] ABSTRACT

Triboelectricity, that is the electrostatic charging of materials by rubbing them against one another, is used to identify particular plastics materials which produce a characteristic charge polarity when rubbed against another known material. An apparatus (24) for carrying out this identification mounts different reference materials (30, 32, 34) so that they can be rubbed against the material (44) to be identified to create electrostatic charges which are then processed by a logic circuit to identify the nature of the sample.

15 Claims, 5 Drawing Sheets

PLASTICS IDENTIFICATION

BACKGROUND OF THE INVENTION

This invention relates to an apparatus and method for identifying different plastics materials. The apparatus and method are particularly (but not exclusively) suitable for use in the plastics industry, for separating plastics components into chemically similar groups, as a first stage in, for instance, the recycling of the plastics materials. In this specification, "plastics" includes both thermoplastic and thermoset materials, whether in the form of solid or foamed material and also includes natural and synthetic rubbers and any composite material which is a combination of any of these materials. The invention is also applicable to such materials in which additives (plastics or non-plastics) have been included.

One field of application is the recycling of motor car components. When a motor car is scrapped, its saleable components such as battery, tyres or radio are removed, usually for use in other vehicles. The metal parts of the scrap car are generally recycled, and what remains is shredded and used as landfill.

The remainder that is used for landfill consists principally of a mixture of plastics materials. For environmental and/or economic reasons it is desirable to be able to recycle such waste plastics material. However, it is not possible effectively to recycle mixtures of waste plastics without first separating the plastics into chemically similar groups or families. Failure to achieve this separation would mean that unknown proportions of different plastics were incorporated in the melt during the reclaim process. The presence of other plastics components in a blend may necessitate changes in processing conditions or lead to unacceptable changes in the physical properties of the finished recycled material.

A requirement for any industrial method of identifying plastics materials for recycling is that the identification is made quickly, preferably in less than one minute per sample. Slow identification speeds would slow down the rate at which components could be grouped according to plastics type, and this can have a significant effect on the economics of any recycling process. In the recycling of motor car components, it is conventional to identify components of value before they are stripped from the car, and if identification of plastics types takes too long, the process of motor car disassembly is slowed down, making it less economic. Currently, however, there is no quick and simple method for identifying the chemical constitution of a plastics component, and therefore no simple method of separating such plastics materials is available.

The number of families of plastics materials which are in common industrial use is relatively small, and in practical terms it is likely to be necessary only to distinguish between about seven or eight different families of plastics. In this specification, the plastics discussed will be referred to by their common acronyms, which are identified as follows:

| PP | Polypropylene |
| PA | Polyamide (nylon) |
| PBT | Poly (butylene terephthalate) |
| POM | Polyoxymethylene/Polyacetal |
| ABS | Acrylonitrile butadiene styrene |
| PET | Poly(ethylene terephthalate). |
| PC | Polycarbonate |
| PVC | Polyvinylchloride |
| PE | Polyethylene |

The physical properties of plastics from any one family can vary considerably depending on the addition of additional components such as fillers and plasticisers, but for the purposes of recycling of plastics, it is of most importance just to be able to identify the plastics family to which a piece of material belongs.

SUMMARY OF THE INVENTION

According to the present invention, there is provided a method for identifying plastics materials, the method comprising the steps of preparing a clean, substantially charge-free surface on a piece of unidentified plastics material, rubbing different areas of the surface with different reference materials, each reference material being of a known, different position in a triboelectric series, and measuring the polarity of the generated electrostatic charges.

A triboelectric series can be derived for a particular reference material by rubbing that material with a series of other materials. If the size and polarity of the electrostatic charge thus generated is measured, the other materials can be ranked relative to each other to produce a series related to that reference material. Other series can be produced in the same way for different reference materials.

By selecting suitable reference materials, it is possible to distinguish between unknown plastics materials. For example if an unknown material is positively charged when rubbed with brass, negatively charged when rubbed with PET and positively charged when rubbed with PP, then an examination of the triboelectric series for the reference materials brass, PET and PP and the plastics types PP, PA, PBT and ABS will show that the unknown plastics material is likely to be ABS. This is not an absolute identification, but if the only materials expected to be present among the materials to be identified are PP, PA, PBT and ABS, then because of the triboelectric series positions of these relative to the choice of reference materials, it is possible to conclude that a particular sample is, for example, ABS. In fact, the method of the invention sorts materials into a certain number of different groups, in this case four groups. In setting the invention up for use, it is first necessary to determine what groups need to be separated from one another, and then to determine the number and identity of reference materials which will achieve that separation.

A look-up table for identifying plastics in this way can be established by recording the charge polarity resulting from the rubbing of known plastics materials against known reference materials. Once the table has been established using known samples of all the plastics to be identified, then it can be used to identify unknown plastics.

The reference materials are preferably provided in the form of rotating bodies, such as rollers, cylinders or discs, and the unidentified material can then be held against the cylinders whilst they rotate to produce the rubbing action. An electrostatic charge is produced as a result of this triboelectric effect. Alternatively however the rubbing action may be produced by an operator moving a reference material relative to the surface of the unidentified material, or by a combination of these two methods.

The generated charges are preferably measured by pick-up heads positioned in contact with or adjacent to the reference materials.

It has been found that it is possible with three reference materials to distinguish between commonly occurring plastics. By taking into account merely the polarity of the electrostatic charge produced, three separate reference materials applied to the same unknown material can produce a theoretical maximum of four different results and by careful choice of the reference materials it is possible to distinguish between different materials such as to make the recycling of the material a viable proposition. However useful distinctions between different plastics materials can be achieved with more than three or with less than three reference materials, to produce different levels of identification.

The invention also provides apparatus for identifying plastics materials, the apparatus comprising a housing, a plurality of different, electrically isolated and electrostatically chargeable reference materials mounted in the housing, means for simultaneously rubbing all the reference materials against a single sample of unidentified plastics material, and pick-up heads for separately measuring the polarity of the electrostatic charge produced at each rubbing location.

The reference materials are preferably mounted in the housing in such a way that a sample of unidentified plastics material can be placed in simultaneous contact with all the reference materials. The reference materials can conveniently be in the form of cylindrical bodies journalled in the housing and drivingly connected to a common drive motor for rotation about a common axis with the bodies being separated on the axis by electrically insulating spacers.

The cylindrical bodies can each have a portion of their periphery presented to a single plane which defines a sample contact face, and the bodies can be carried in the housing on bearings which can be resiliently displaced from the sample contact face.

Where the reference materials are rotatable bodies, the pick-up heads can comprise brushes (of conductive material) in electrical contact with the reference materials or can comprise conducting pick-ups positioned in close proximity to (but not touching) the reference materials, so that a charge on the reference material induces an opposite charge on the pick-up head. Where the reference materials are stationary relative to the housing, the pick-ups can be directly connected thereto.

The housing is preferably small enough to be held in the hand, so that it can be readily carried around and held against a plastics component to identify the material of that component. The housing may include the power source necessary to operate the apparatus and may have a display to indicate the type of plastics identified. Alternatively, the housing may be connected by a conductive lead to a power source and/or to a signal processor which has such a display. The display may comprise a series of lights corresponding to the number of different material groups which can be identified, with each light being labelled with the name of the corresponding material group. An additional light may be provided to denote an insufficient rubbing action, so that the operator repeats the action.

The apparatus may also include a reset facility by which any charge remaining on the reference materials is discharged, before the apparatus is used to take a reading. This discharge process can use ions or an electrically conductive brush.

The apparatus may include a component intended to periodically clean the reference material surfaces. This component could be incorporated in a cap intended to be placed over the reference materials when the apparatus is not being used.

The invention can also be used to simply distinguish between two different plastics materials, and to do this the invention also provides a method for identifying plastics materials, the method comprising the steps of preparing a clean, substantially charge-free surface on a piece of unidentified plastics material, rubbing the surface with a reference material, and measuring the polarity of the generated electrostatic charge.

In this form, the invention also provides apparatus comprising a housing, an electrically isolated and electrostatically chargeable reference material mounted in the housing, means for rubbing the reference material against a single sample of unidentified plastics material, and a pick-up head for measuring the polarity of the electrostatic charge produced.

In these simple forms of the invention, the features set out above relating to constructional features and analysis of the charge readings produced can also be used.

BRIEF DESCRIPTION OF THE DRAWINGS

The invention will now be further described, by way of example, with reference to the accompanying drawings, in which.

DETAILED DESCRIPTION OF THE PREFERRED EMBODIMENTS

Figure 1:
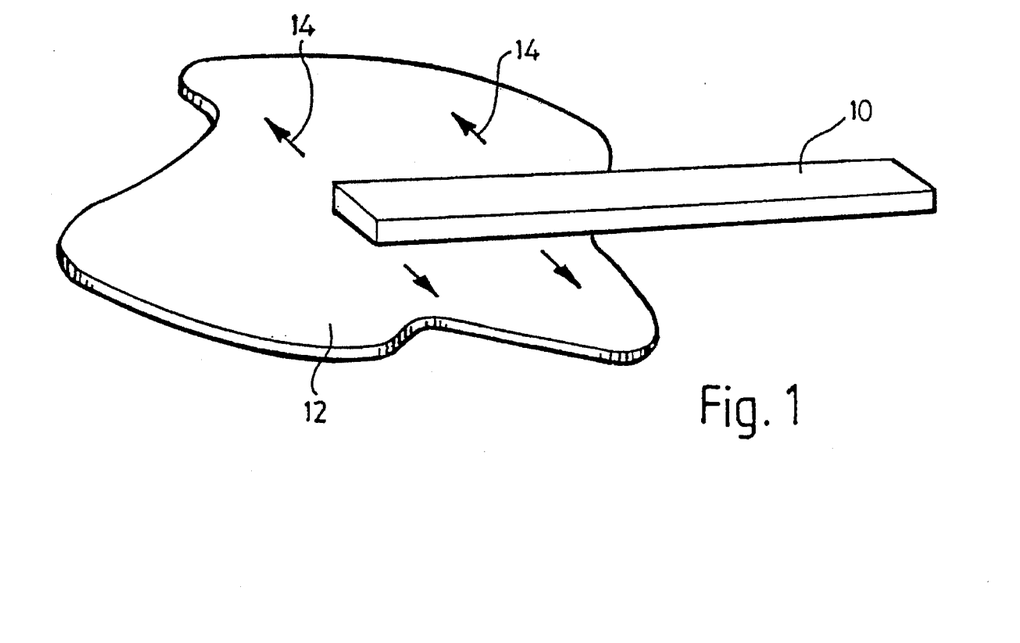
FIGS. 1 and 2 illustrate a simple electrostatic experiment on which the present invention is based.
Figure 2:
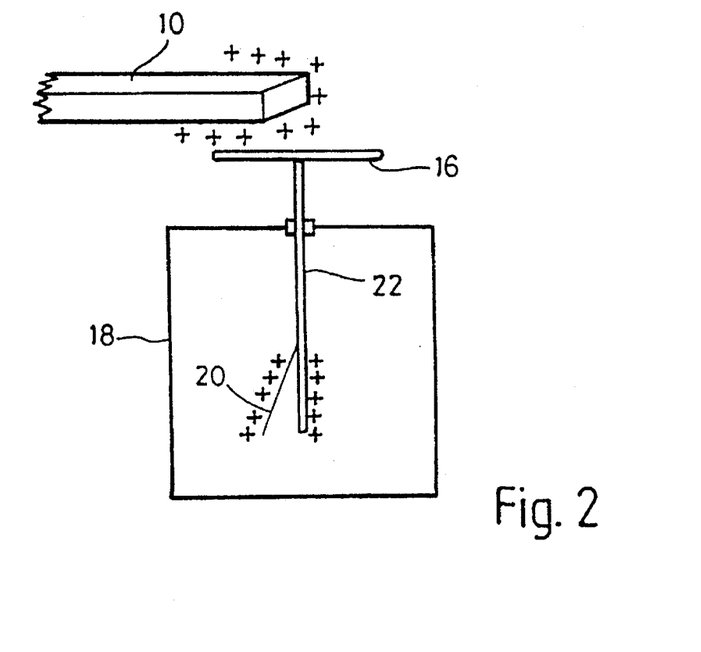

When two non-conducting materials are rubbed against one another an electrostatic charge is produced. FIG. 1 shows a plastics rod 10 being rubbed over a plastics plate 12 as indicated by arrows 14. This produces an electrostatic charge on both the plate 12 and the rod 10, of equal magnitude but of opposite sign. The traditional way of demonstrating that this charge exists is to hold the end of the rod 10 close to the pick-up plate 16 of an electroscope 18 as illustrated in FIG. 2. The electrostatic charge on the rod 10 causes a migration of charge in the electroscope leading to the electroscope leaf 20 being repelled from the stem 22 as a result of the repulsion effect of like electrostatic charges.

The production of an electrostatic charge in this way is a result of the phenomenon of triboelectricity. Depending on the nature of the two materials, the charge on one will be positive and the charge on the other will be negative, or vice versa.

Table 1 then shows that four materials identified in the table as Nylon, ABS, PP and PE can be differentiated from one another by comparing merely the polarity of a pick-up head relative to a sample of the material in each case.

TABLE 1

| Head Material | ACRYLIC | COPPER | PVC |
| --- | --- | --- | --- |
| Nylon sample | − | − | − |
| ABS sample | + | − | − |
| PP sample | + | + | − |
| PE sample | + | + | + |

Using the results from this Table, it is possible to distinguish between Nylon, ABS, PP and PE using only the direction of polarity and ignoring any quantitative charge value.

FIGS. 3–9 illustrate an apparatus for doing this. The apparatus has a housing 24 of a suitable size to be held in the hand. The housing has a head unit 26 and in the head unit three different reference materials are mounted in a manner to be described. The head unit 26 also includes a set of indicator lights 28 (there are five lights in the embodiments shown). These lights may be light emitting diodes. The housing 24 will include a drive motor 70 for operating the apparatus together with electronic circuitry for evaluating the signals generated. The apparatus may be powered by batteries contained in the housing (with the batteries being recharged using a conventional battery charging device), or the apparatus may be connected by a lead (not shown) to a power source and/or to remote electronic circuitry.

Figures 3, 4, 5:
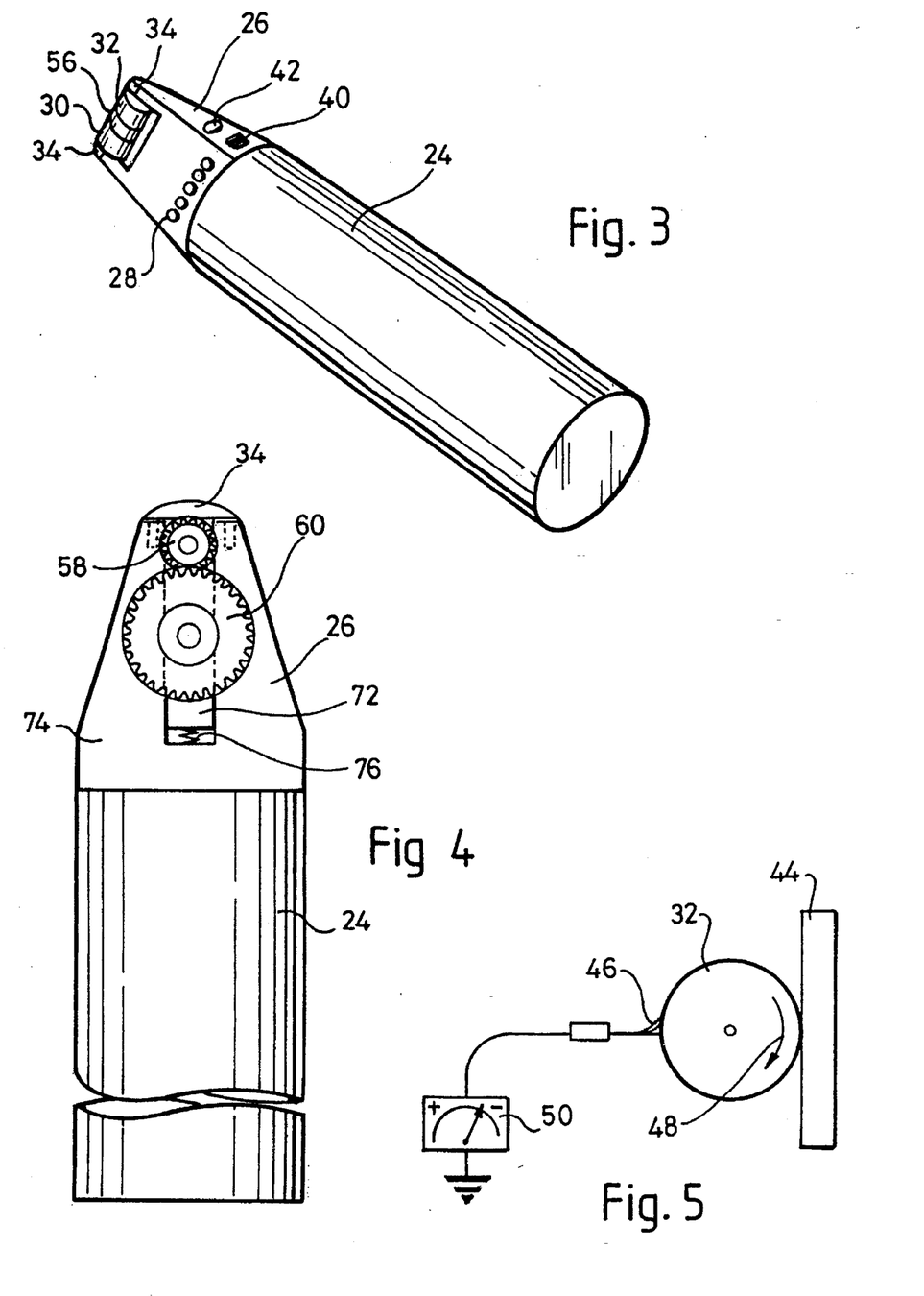
FIG. 3 is a perspective view of a first embodiment of an apparatus in accordance with the invention.
FIG. 4 is a side view of the apparatus of FIG. 3 with parts of the housing removed.
FIG. 5 is a diagram illustrating operation of the apparatus.

The head unit 26 carries two cylindrical reference material bodies 30, 32 mounted for rotation on a common axis. The bodies are rotated by the motor 70 contained within the housing 24 and connected to the bodies through a system of gears.

In addition to the rotatable cylindrical reference material bodies 30, 32, the head unit carries two fixed reference material bodies 34. The bodies 30, 32, 34 are made of reference materials which have a different position in a triboelectric series.

The housing also incorporates an on/off switch 40 and a reset button 42.

In use, the reference material bodies 30, 32, 34, are made to rub across a sample of the material being tested. This rubbing could be achieved, in the case of the rotatable bodies 30, 32, by simply holding the head against a sample. However because the reference material bodies 34 are fixed to the head, it is necessary to move the head across the sample. This is illustrated in FIG. 5, where the sample being tested is indicated at 44 and one of the reference material bodies is indicated at 32. A conductive brush 46 wipes against the surface of the body 32 remote from the sample 44. As the body 32 rotates in the direction of the arrow 48, the friction between the surface of the body and the sample 44 produces a charge on the surface of the body, and this charge is picked up by the brush 46 and is conducted to a charge meter indicated at 50.

Figure 6:
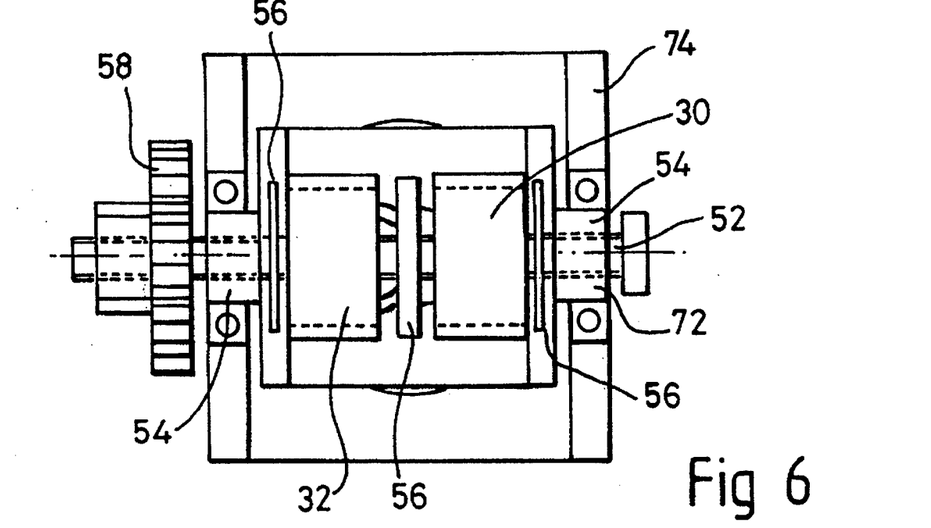
FIG. 6 is an end view showing the mechanical arrangement of the reference materials in the housing.
Figure 7:
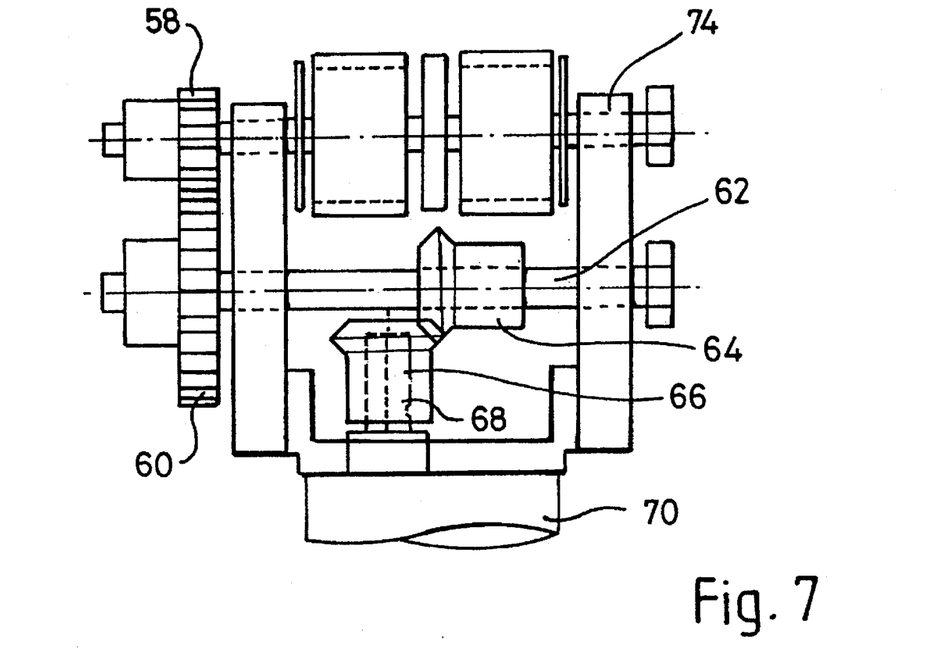
FIG. 7 is a side view corresponding to FIG. 6.

FIGS. 6 and 7 show the mechanical arrangement of the cylindrical bodies 30, 32 in more detail. The bodies 30, 32 are mounted on a common shaft 52 carried in bearings 54. Shielding plates 56 are mounted on the shaft 52 to prevent charge leakage. At one end of the shaft 52 a pinion 58 is fitted and, as can be seen from FIG. 7, the pinion 58 is in mesh with a further pinion 60 mounted on an intermediate shaft 62. A bevel gear 64 fixed on the shaft 62 meshes with a corresponding bevel gear 66 on the output shaft 68 of the drive motor indicated schematically at 70.

The shafts 52 and 62 are mounted in a yoke 72, and this yoke is supported in slots in a pair of end cheeks 74 of the head 26. The motor 70 is also secured to the yoke which is urged towards the front end of the head by springs 76 (see FIG. 4), and when the rollers are placed in contact with a surface 44 they are pressed back into the housing, against the force of the spring 76, to ensure that they make good contact with the sample 44.

In use, the apparatus is switched on, so that the cylindrical reference material bodies 30, 32 start to rotate. The reset button 42 is depressed, and this ensures that any charge initially present on the bodies 30, 32 or on the fixed reference material bodies 34 is completely discharged. A surface on the sample 44 is prepared by cleaning it of any dirt, and then discharging the surface for example by wiping it with alcohol or by using some form of abrasive cleaner. The apparatus is then pressed against the surface and moved relative to the surface to produce friction between the fixed bodies 34 and the surface. As a result of this movement, an electrostatic charge is created between the sample and the fixed bodies. At the same time the cylindrical bodies 30, 32 are rotating against the surface and so charge is built up on those surfaces also. The apparatus then makes use of the concept that the charge Q is a function of capacitance C and voltage V. The relationship between these parameters can be expressed as Q=CV. Therefore if the voltage across a capacitor and the value of the capacitor are known, the charge Q may be measured. By measuring the polarity of the charge resulting on each reference material from the movement of that reference material against the sample, a set of results can be produced which can be compared with a stored set of results corresponding to Table 1, and using this table a result can be achieved as to the type of material of the sample 44. In accordance with this result, one of the indicator lights 28 will light up. These lights will be labelled each with the name of one plastics family so that if, for example, the polypropylene light lights up, then this is an indication that the sample 44 is made of polypropylene.

If the operator does not move the apparatus across the sample correctly or for sufficient distance for an accurate reading to be obtained, then the fifth light 28 will light up indicating an invalid reading which should be repeated.

Figure 8:
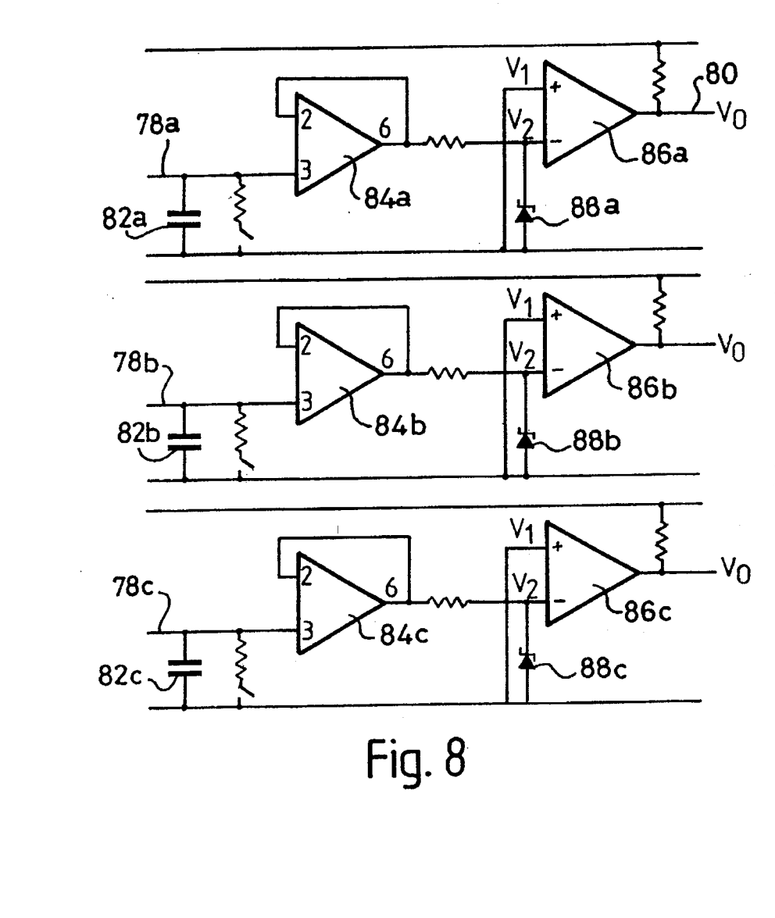
FIGS. 8 and 9 illustrate, respectively, a comparator stage and a logic stage for producing an output from the apparatus of the invention.
Figure 9:
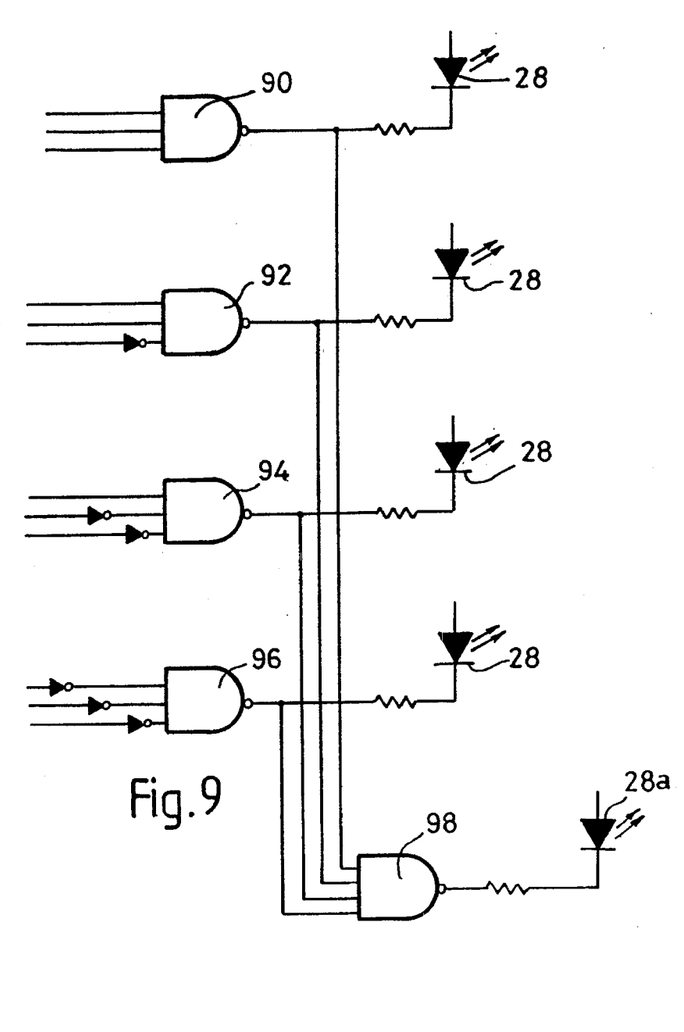

The circuitry used to achieve this measurement is indicated in FIGS. 8 and 9. FIG. 8 shows three comparator stages which receive and process the signals from the three reference material bodies 30, 32, 34. The charge on the reference material body 30 is applied as an input voltage on the signal line 78a; the charge on the reference material body 32 is applied as an input voltage on the signal line 78b and the charge on the reference material body 34 is applied as an input voltage on the line 78c. The electrostatic charge generated in each case will charge a capacitor 82a, 82b, 82c and this charge is fed into a buffer amplifier 84a, 84b, 84c. A comparator 86a, 86b and 86c has two input voltages $V_1$ and $V_2$. The first input voltage $V_1$ is held at a constant level (usually ground potential) as a constant reference, while the other voltage $V_2$ is a varying signal dependent upon the electrostatic charge.

The voltage transfer characteristics of the comparator circuit are as follows:

A constant output 0 (zero) is obtained if the output voltage, ie the second input voltage subtracted from the reference voltage, is less than 0 (ie negative).

A constant output 1 (one) is obtained if the output voltage, ie the second input voltage subtracted from the reference voltage, is greater than 0 (ie positive).

A Zener diode 88a, 88b, 88c is used to protect the input of the comparator 86a, 86b, 86c from overloading.

In the logic stage shown in FIG. 9, four logic gates 90, 92, 94 and 96 are used, each corresponding to one of the four indicator lights 28, and a fifth logic gate 98 corresponds to the "invalid reading" indicator light 28a.

For the PE logic circuit to be activated, a three input NAND gate 90 is used. Therefore the output will always be HIGH (logic 1) unless all three inputs to the NAND gate are HIGH.

For the PP logic circuit to be activated, a similar three input NAND gate 92 is used. However the #3 input has a NOT gate which inverts the input. Therefore the output will always be HIGH (logic 1) unless the #1 and #2 inputs are HIGH, and the #3 input is LOW (logic 0).

For the ABS logic circuit to be activated a three input NAND gate 94 is used, however the #2 and #3 inputs to the gate are inverted by NOT gates. Therefore the output will always be HIGH, except when the #2 and #3 inputs are LOW (logic 0) and the #1 input is HIGH (logic 1).

For the Nylon logic circuit to be activated a three input NAND gate 96 is used with all three inputs to the NAND gate inverted (ie effectively an AND gate). The logic level will always be HIGH (logic 1) unless all inputs to the gate are LOW (logic 0).

For the Undetermined circuit a four input NAND gate 98 is used with the inputs originating from the previous four logic gate outputs. If the outputs of all of the previous gates are at a HIGH logic level (logic 1) the output of the gate 98 will go LOW (logic 0).

By operating in this way, a simple YES/NO output is achieved which requires no previous knowledge to interpret it. The operator will simply see that a particular light lights up and he will then know that the plastics material which he has been testing is of the composition indicated and he can then deal with the component in accordance with that information.

Figure 10:
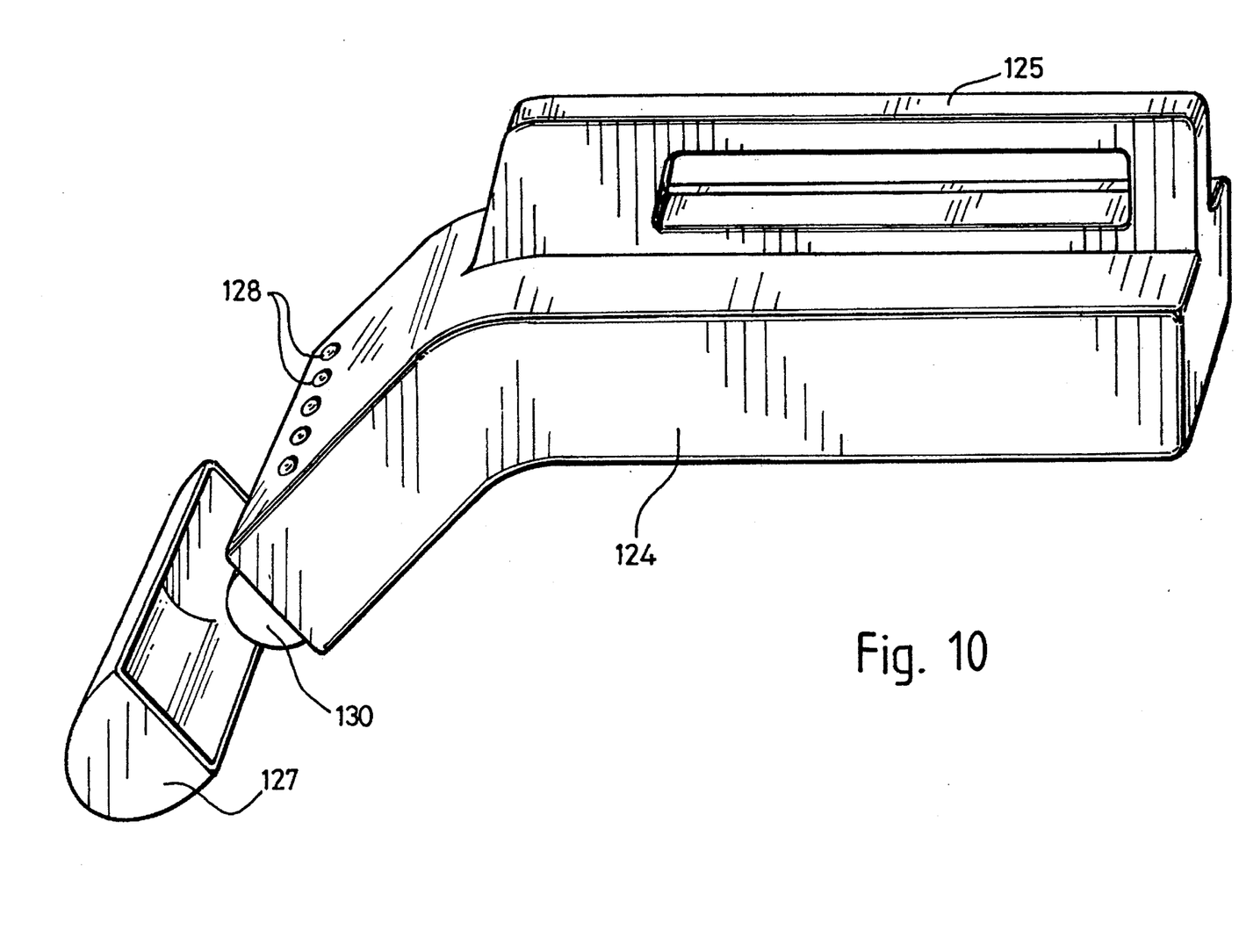
FIG. 10 illustrates a second embodiment of an apparatus in accordance with the invention.

FIG. 10 shows an alternative form of apparatus with a housing 124 and reference material rollers, one of which is indicated at 130. The housing has a handle 125 and indicator lights 128. The apparatus is also provided with a cap 127 which fits over the reference material heads when the apparatus is not in use. The inside of the cap may contain cleaning and/or discharging components and the reference materials may be rotated with the cap in place, to effect cleaning and/or discharging.

Alternatively, in either the first or the second embodiment, cleaning and/or discharging components could be provided within the housing 24, 124. These components could take the form of an abrasive pad and/or an alcohol swab which could be moved against the reference materials e.g., heads by pressing a suitably mounted lever.

It will be clear to those skilled in the art that the housing 24 can take a wide variety of different forms. It is desirable that it should be readily portable so that it can be taken to the sample to be identified rather than vice versa. It may be necessary to periodically clean the surfaces of the reference materials, and so a cap for the apparatus can be provided which can incorporate cleaning and discharging components.

In a preferred embodiment a fixed reference material body 34 is made of copper and the two rotating bodies 30 and 32 are made respectively of acrylic and PVC.

An apparatus as described can greatly facilitate the process of recycling plastics components, because it makes it possible for them to be easily identified into different plastics families, for the appropriate recycling steps.

The particular materials which the particular units can identify depends on the nature of the reference material bodies on the apparatus. In order to be able to identify different or additional materials, it is only necessary to select a different set of reference materials so that, when all the materials to be identified and all the reference materials are listed in a common triboelectric series, a reference material falls between each pair of materials to be identified. For example in the case of the materials described here the triboelectric series could be represented as follows:

```
         −ve end
         ... PE    (Sample)
   PVC         (Reference)
         ... PP    (Sample)
   Copper      (Reference)
         ... ABS   (Sample)
   Acrylic     (Reference)
         ... PA    (Sample)
         +ve end
``` and it will be clear that this series can be extended, varied or contracted to identify different sample materials.

We claim:

1. A method for identifying plastics materials, the method comprising the steps of preparing a clean, substantially charge-free surface on a piece of unidentified plastics material, rubbing the surface with a plurality of reference materials to generate a plurality of electrostatic charges, each reference material being of a known, different position in a triboelectric series, measuring the polarity of the generated electrostatic charges, and comparing the polarity measurements with polarity measurements of known plastics materials in the triboelectric series to identify the previously unidentified plastics material.

2. A method as claimed in claim 1, wherein the reference materials are provided in the form of rotating bodies and the unidentified material is held against the bodies whilst they rotate.

3. A method as claimed in claim 1, wherein the generated charges are measured by pick-up heads mounted adjacent to the reference materials.

4. A method as claimed in claim 1, wherein three different reference materials are used.

5. A method as claimed in claim 1, further comprising the step of generating a signal based on the polarity measurements, wherein the generated signal identifies the previously unidentified plastics material.

6. Apparatus for identifying plastics materials, the apparatus comprising a plurality of different electrically isolated and electrostatically chargeable reference materials, means for simultaneously rubbing all the reference materials against a single sample of unidentified plastics material, and pick-up heads for separately measuring the polarity of the electrostatic charge produced at each rubbing location.

7. Apparatus as claimed in claim 6, wherein the reference materials are mounted in such a way that a sample of unidentified plastics material can be placed in simultaneous contact with all the reference materials.

8. Apparatus as claimed in claim 6, wherein at least one of the reference materials is in the form of a cylindrical body journalled in a housing and drivingly connected to a drive motor for rotation about an axis.

9. Apparatus as claimed in claim 8, including at least two reference materials in the form of cylindrical bodies journalled in a common housing and drivingly connected to a common drive motor for rotation about a common axis, with the bodies being axially offset and separated by insulating spacers.

10. Apparatus as claimed in claim 8, wherein at least one of the reference materials is in the form of a body fixed in the housing.

11. Apparatus as claimed in claim 10, wherein the bodies each have a portion of their periphery presented to a sample contact face, and the rotatable bodies are carried in the housing on bearings which can be resiliently displaced relative to the fixed body.

12. Apparatus as claimed in claim 6 wherein the pick-up heads pick up charge from the reference materials.

13. Apparatus as claimed in claim 12, wherein the pick-up heads comprise brushes in electrical contact with the reference materials.

14. Apparatus as claimed in claim 12, wherein the pick-up heads are positioned in close proximity to the reference materials, so that a charge on the reference material induces an opposite charge on the pick-up head.

15. Apparatus as claimed in claim 6 including a comparator circuit for comparing the polaritities of the electrostatic charges produced at each rubbing location with stored data, and a logic circuit for identifying the previously unidentified plastics material from the comparator output.

* * * * *